United States Patent [19]
Kruger

[11] Patent Number: 5,927,982
[45] Date of Patent: Jul. 27, 1999

[54] THREE DIMENSIONAL GUIDANCE SYSTEM FOR DENTAL IMPLANT INSERTION

[76] Inventor: Bernard M. Kruger, 5 Natalie Dr., West Caldwell, N.J. 07006

[21] Appl. No.: 09/162,879

[22] Filed: Sep. 29, 1998

[51] Int. Cl.⁶ ................................................. A61C 13/36
[52] U.S. Cl. .......................................... 433/215; 433/213
[58] Field of Search ..................................... 433/213, 215

[56] References Cited

U.S. PATENT DOCUMENTS

| | | | |
|---|---|---|---|
| 4,878,841 | 11/1989 | McCulloch et al. | 433/215 |
| 5,320,529 | 6/1994 | Pompa | 433/215 |
| 5,401,170 | 3/1995 | Nonomuro | 433/215 |
| 5,545,039 | 8/1996 | Mushabac | 433/215 |
| 5,662,476 | 9/1997 | Ingber et al. | 433/213 |
| 5,706,814 | 1/1998 | Nonomuro | 433/215 |
| 5,769,636 | 6/1998 | Di Sario | 433/213 |

Primary Examiner—Paul J. Hirsch
Attorney, Agent, or Firm—Ralph T. Lilore

[57] ABSTRACT

A three dimensional guidance system for locating the correct or optimal angles of implant insertion into a dental patient's jawbone is described. The optimum angles, depths, and positioning are obtained as follows: a surrogate of the patient's mouth is provided in the form of stone model of the intended implant region with the edentulous area being exposed, a diagnostic work-up, usually in wax, of the stone model, and perforce of the patient's mouth, is produced and fitted with a pontic tooth or teeth in the proper occlusal relationships, a three-dimensional guidance system in the form of a drill press containing a platform or table movable through all directions about a fixed point defined by the drill point. In practice, the radiographic guide is placed on the patient and a CT-scan taken. Since the radiographic guide had previously been provided with radio-opaque landmarks, the resulting images will show specifically those landmarks in relation to the anatomical features that must be considered in drilling the osteotomy. From the images, the relevant depth and angular measurements are taken.

5 Claims, 2 Drawing Sheets

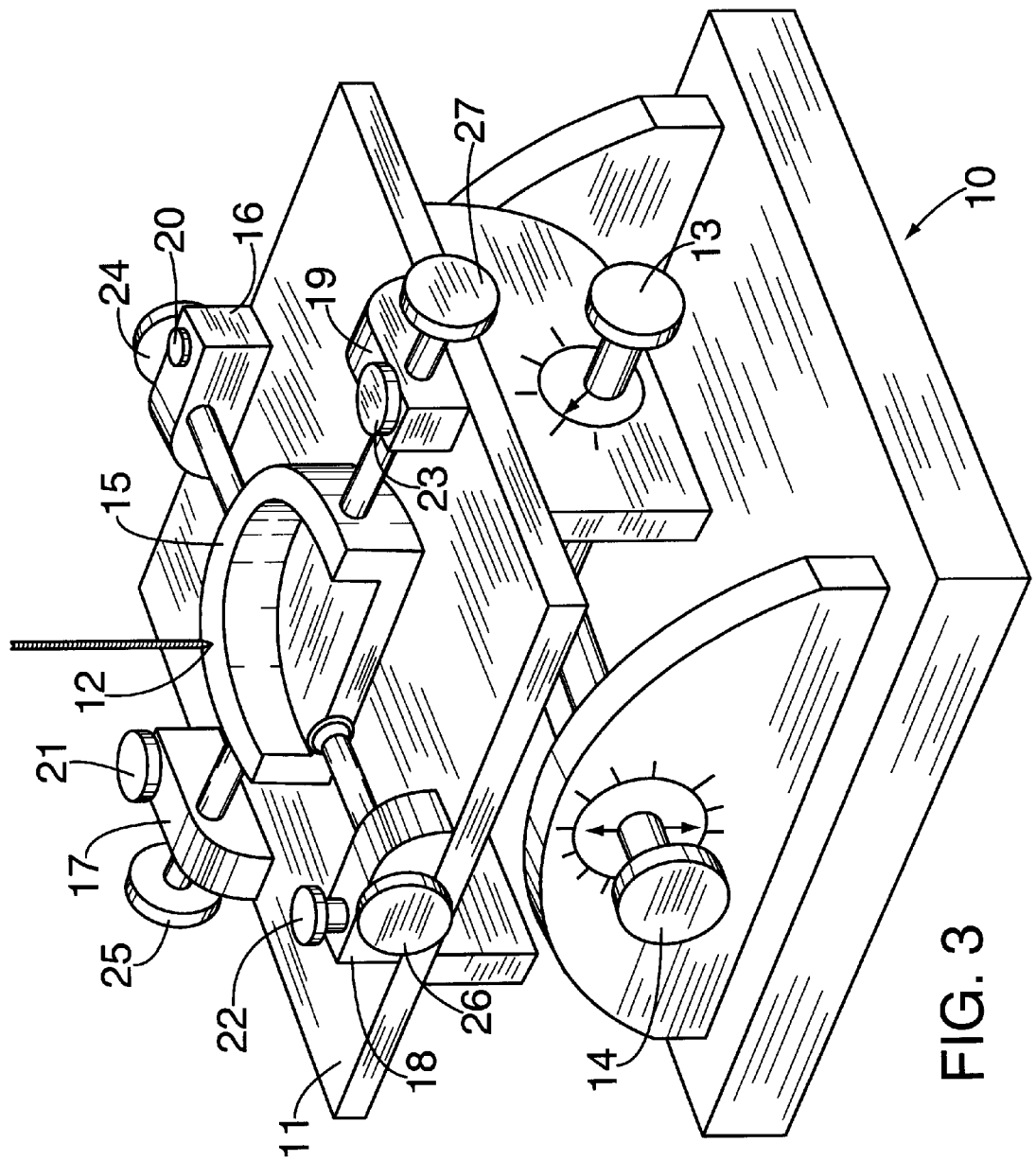

THREE DIMENSIONAL GUIDANCE SYSTEM FOR DENTAL IMPLANT INSERTION

This invention relates to dental implants and more particularly to a three dimensional guidance system for locating the correct or optimal angles of implant insertion into the patient's jawbone.

Most clinicians agree that optimum dental implant positioning requires balancing the inter-relationship of occlusion, quality and quantity of residual bone at the implant site, and anatomical requirements such as nerve and sinus to locations. In the past, surgical guides and CT-scans have been recommended to accomplish this objective. There has not been any direct correlation of the occlusion on the cross sectional images of the scan with other parameters using the past techniques.

Vertical gutta percha markers have been placed within the surface contours of pontic teeth, depicting possible fixture sites within a diagnostic radiographic guide but this has not been satisfactory either.

In an attempt to improve this correlation, the art has attempted to use a radiographic guide constructed by using a vacuum formed shell of the planned occlusion and applying a radio-opaque lining to the shell. The CT-scan would be obtained with the radiographic guide in position.

Despite these attempts at improving the technique, however, when the actual surgery is performed, the three dimensional orientation of the implant is still nevertheless based on the clinical judgment of the clinician in consideration of his/her perception of the three dimensional aspects based on the available information. The lack of objective precise guide marks presents not only surgical risks, but can lead to less than optimum implant positioning which can contribute to implant overload. An objective of this invention is to provide novel techniques, instruments, and apparatuses which enable the optimum three dimensional pre-planned positioning of each individual implant, utilizing a three dimensional, drill guidance system.

Utilization of the process and apparatus of the present invention enables the optimum positioning of the dental implant irrespective of the orientation of the underlying bone structure and gives due consideration for the buccal-lingual and anterior-posterior orientation of the surrounding teeth as well as the presence of critical anatomical features and structures such as sinuses, nerves, adjacent roots, and the like.

Prior to the invention as described herein, the clinician was relegated to using judgment in attempting to scale off distances and angles from a CT-scan without having precise landmarks with which to measure those angles and critical structures. The present invention, therefore, provides the means by which a) appropriate landmarks can be introduced into the x-ray so that the resulting images will reflect the appropriate horizontal and vertical orientations in consideration of proper occlusal surfaces and other angular orientations as described above and b) those landmarks are transferred to a stone cast of the mouth impression and c) a three dimensional guidance system enables the transfer of the measured angles and depths to the patient.

SUMMARY OF THE INVENTION

According to the invention, there are three essential elements to be provided in order to obtain the predetermined, appropriate, and hopefully the optimum angles, depths, and positioning. In general, these involve the following:

1. A surrogate of the patient's mouth is provided in the form of stone model of the intended implant region with the edentulous area being exposed. This surrogate, typically called a stone cast or stone model, is produced by well-known techniques.

2. A diagnostic work-up, usually in wax, of the stone model, and perforce of the patient's mouth, is produced and fitted with a pontic tooth or teeth in the proper occlusal relationships. This will, when modified as described below, serve as the radiographic guide and when further modified, will be the basis of the surgical guide used to produce the osteotomies necessary for the pre-determined implant location and orientation. The radiographic guide fits over both the stone model and the patient's teeth.

3. A three-dimensional guidance system in the form of a drill press containing a platform or table movable through all directions about a point defined by the drill point. That is to say, that the table is tiltable to achieve any angle in the antero-posterior direction and the medial-lateral direction as well as in vertical and horizontal directions.

In practice, the radiographic guide is placed on the patient and a CT-scan taken. Since the radiographic guide had previously been provided with radio-opaque landmarks, the resulting images will show specifically those landmarks in relation to the anatomical features that must be considered in drilling the osteotomy. From the images, the relevant depth and angular measurements are taken.

The radiographic guide is then modified by shortening the pontic teeth and cutting a portion of the guide underneath those teeth so that when the guide is placed on the stone cast or on the patient, the residual ridge crest can be visualized. The shortened pontic teeth will present less drilling distance as will be seen below.

The modified radiographic guide is placed onto the stone model and then using the measurements obtained from the CT-scan, the points of entry onto the residual ridge crest for each implant underneath the pontic tooth is marked on the stone model.

The model is next placed on the table of the three-dimensional guide drill press and secured thereto with securing means. The drill point is brought down to exactly the marked spot on the ridge crest of the stone cast. The correct angles from the CT-scan are then set by manipulation of the table around that drill point center mark on the ridge crest. The drill point is then raised and the radio-graphic guide then re-inserted onto the now secured and properly angled stone model. The drill point is then lowered to meet the radiographic guide and a pilot hole drilled through the pontic tooth to meet the alveolar ridge exactly at the point marked on the stone cast. The angle of the drill relative to the tilted stone cast on the table will be the precise angle obtained from the CT-scan with the following proviso. Because it is the stone cast being manipulated as opposed to the drill point, the angle drilled will be in the direction opposite (i.e. 180°) the angle taken from the CT-scan. Thus, if the scan shows as a buccal tilt of six degrees, for example, the table is tilted in the lingual direction (instead of the buccal direction) six degrees to give the correct orientation of the implant.

Once the pilot hole is drilled through the pontic tooth and the process repeated for any other pontic teeth, the radiographic guide is removed, fitted with an appropriate guide tube through the pilot hole, and then is available for placement on the patient and as such will constitute the surgical guide. Any drilling through the guide hole therefore will be at the precise angles set on the guidance system, the only consideration now being the depth to which the osteotomy is drilled.

BRIEF DESCRIPTION OF THE DRAWINGS

FIG. 3 is a pictorial representation of the dual axis three dimensional guidance table for obtaining the proper angles in the surgical guides to obtain the appropriate implant angles subsequently on the patient.

DETAILED DESCRIPTION

Figure 1:
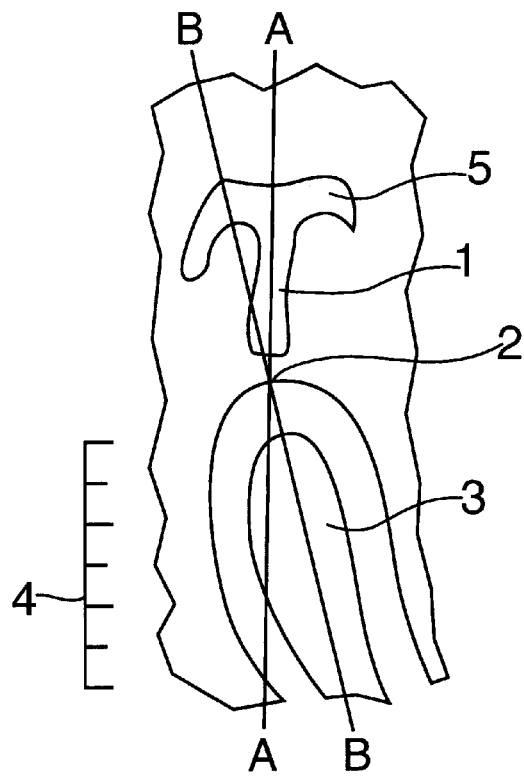
FIG. 1 is a drawing taken from a cross-sectional image taken off a CT-scan showing location of the vertical orientation pin and the radiographic guide in relation to bone into which an implant will be inserted.

The following description provides details used to obtain the benefits of the invention some of which are well-known to the art and are done in the ordinary manner. They are described here to give the context in which the novel elements of the invention are presented.

1. Preparation of Radiographic Guide With Radiopaque Landmarks to Provide Spatial Orientation to the Vertical Plane.

First, the usual mouth and tooth impression and stone cast are prepared from the patient making certain that there is particular reference to the implant site and the surrounding occlusal surfaces. This is followed by the preparation of a radiographic guide which is fitted with pontic teeth that represent the prostheses which will ultimately sit on the implant. Those skilled in the art will be familiar with the preparation of both the overall mouth impression and the radiographic guide with pontic teeth in the proper occlusal relationship for the patient.

An element of the invention at this point is to place in the pontic teeth a radio-opaque landmark which will be subsequently located on a CT-scan (or any other appropriate imaging system) which will orient the images to the center of the pontic tooth and will identify to the clinician the vertical axis (relative to the occlusal plane) of the particular image of the CT-scan.

In the preferred embodiment of the invention, we prefer to drill a hole into the center of the pontic tooth in the vertical direction to the occlusal plane and to fill that hole with a to radio-opaque material. In addition, the pontic teeth are also covered with a thin radio-opaque surface so that on subsequent evaluation of the CT-scan, the outline of the pontic teeth will be clearly shown in relation to vertical and in relation to the occlusal plane and surfaces needed for optimum placement of the implant.

At this point, a channel about 1.5 mm wide and 1.5 mm deep corresponding to the residual ridge crest is cut into the gingival surface at the underside of the radio-graphic guide under the pontic tooth. The channel is then filled with a radio-opaque material so that it may be clearly seen on the CT-scan. This will locate the residual ridge on the CT-scan.

2. Preparation of Images Locating Plane Vertical To Occlusal Plane and Relevant Structures.

Second, the patient is then fitted with the so-modified radiographic guide and subjected to a CT-scan. The purpose at this point is to locate slices or images, preferably at 1 mm intervals, of the relevant area and to locate the vertical axis relative to the horizontal occlusal plane, locate the center of the pontic tooth, the tooth outline and the residual ridge crest and its intersection with the pontic tooth centerline, and locate the position of the jawbone and the critical anatomical structures in the surrounding area such as nerves, sinuses, adjacent tooth roots, and the like.

3. Locating Optimum Location For Implant

Third, from the resulting CT-scan, the clinician identifies the location of the elements described above and assesses the quality of the bone as to whether it is weak or strong in a given area, whether it is narrow or wide in the cortical bone area, whether it has a longer depth or shorter depth to receive an implant. In addition, he or she also assesses the quality and direction of the medullary bone to decide whether modifications in tilt of the potential implant should be made in one direction or another so as to optimize the location of the implant in the strongest area of bone that is accessible to the clinician in consideration of the presence of the other anatomical structures.

4. Determine Location Angles and Depths of Implants

Fourth, from those qualitative aspects as they appear on the CT-scan, the clinician then decides on the optimum location and orientation of the putative implant by considering the buccal-lingual tilt, the anterior-posterior tilt, the orientation of adjacent teeth, the depth of roots, the width of bone and probable depth of the implant (to avoid perforation of the bone by the implant) and nerves and sinuses. The clinician is aided in this assessment and determination by having the ability to make a direct measurement off the CT-scan of the buccal-lingual tilt, the anterior-posterior tilt, and the maximum depth of the implant.

Knowing the pontic center orientation from the radiographic marker previously inserted into the pontic teeth and knowing the outline of the pontic tooth because of the placement of radio-graphic material thereon and the location of the residual ridge crest, the clinician can determine the proper angles of buccal-lingual and anterior-posterior tilt from the scan. He/she could also determine the depth to which the implant must or should be placed and how far away it win be from the critical elements. He/she can actually take direct measurements in millimeters and direct angular measurements from the CT-scans and record those for use as described below.

5. Preparation of Surgical Guide by Transfer of Images Onto Radiographic Guide

Fifth, having obtained the measurements and location in umber four above, the clinician transfers the measurements to he radiographic guide which are then transferred to the stone model. A convenient and preferred way to do this according to he invention is 1. The gingival outline at the pontic tooth of the radiographic guide is transferred to the stone cast.
2. The pontic tooth is reshaped to the residual ridge crest line and that line transferred to the stone cast.
3. The extension of the center line of the pontic tooth on the guide is located at its intersection with the residual ridge crest line and the stone cast marked accordingly.
4. The gingival portion of the pontic tooth is cut back 2–3 mm so that the residual ridge crest on the stone cast is visualized when the cast is in place.
5. The occlusal surface of the pontic tooth is cut down to reduce the length of drill needed.

To convert the so-modified radiographic guide into a surgical guide according to the invention, a drill guide tube must be properly positioned in the pontic tooth at the optimum angles determined from the CT-scan and will ultimately guide the drill into the bone when the osteotomy is performed. According to one embodiment of the invention this is achieved as follows:

The stone cast is placed on a drilling press adapted to contain a three dimensional orientation table. (See FIG. 3). The table is movable in the horizontal x-y directions and the vertical direction, is tiltable about a point (the drill point usually) in the horizontal plane to obtain virtually any combination of angles in the anterior-posterior and buccal-lingual directions. Such devices have been used in industrial applications but to our knowledge have never been used before in the dental field. Before the guide is placed on the cast, the intercept of the center of the pontic tooth with residual ridge is marked on the cast, the table is manipulated through the anterior-posterior and buccal-lingual angles determined from the CT-scan about that point with care being taken to provide the opposite angle orientation as noted above. The guide is then replaced and a 3.0 o.d. mm drill inserted to drill a pilot hole through the pontic tooth to meet the marked point on the ridge crest of the cast.

As a result of setting the cast at the appropriate angles, the drilling of the 3 o.d. mm pilot hole will be at precisely the angles necessary to obtain an osteotomy in the jawbone at the very angles determined from the CT-scan. Thereafter, a 1.6 mm i.d. drill guide tube is inserted into the 3 mm o.d. pilot hole in the pontic tooth and fixed into position.

Once the guide tube has been inserted into the drilled guide hole in the pontic tooth at the angles drilled as described above, the radiographic guide carrying the guide tube is then considered to be the surgical guide which may then be used on the patient.

In practice, before placement of the guide, the patient's gingiva in the area of the implant are flapped back to expose the bone which will ultimately receive the implant. The surgical guide may be modified prior to placement in the patient's mouth so that the bottom edges will not actually hit the bone. Once the surgical guide is applied onto the patient's teeth, the guide tube is directly above or even contacting the necessary point of entry into the ridge crest. Drilling in gradually widening widths through the guide tube can commence.

Because the proper angle of the drill guide tube into the pontic tooth has been obtained, that angle will be continued into the jawbone so that the proper angle of the implant will be obtained. Since the depth of the implant has already been pre-determined, the drill will be inserted no further than that pre-determined depth using either techniques known in the art or a new type of drill described in co-pending U.S. application Ser. No. 08/685,920.

Once the first osteotomy has been achieved at the proper angles, the guide is removed and increasing widening drills at half millimeter intervals from the 1.6 mm up to the 3.6 level or higher are used to widen the osteotomy to the point at which the implant can be screwed. To avoid or minimize wobble, it is preferred to use drills which have the first portion of the inserted end equal to the diameter of the last drilled osteotomy followed by a cutting portion having the next desired widening diameter.

With the implant in place, a proper prosthetic tooth can be fitted, which because of the presence of the pontic tooth in the original impression, will be precisely and accurately located to give the proper occlusal relationship.

The preferred mode of preparing the various elements employed in the invention are as follows:

Radiographic Guide Fabrication

Impressions are obtained and a diagnostic wax up is created on the models derived from the previously taken impression and stone casts constructed. A digital wax-up is produced which includes the pontic areas and then lingual, palatal, buccal, and occlusal wax exteriors are added to form the final wax-up. The wax-up is then flashed and processed using standard fabrication techniques. It is recommended that the casts be occluded to provide indentations of the opposing arch in order to increase stability of the radiographic guide during the CT-scan procedure. After the acrylic guide is processed, it is removed and re-fitted to a stone cast containing the edentulous spaces.

Pontic orientation channels: The radiographic guide is constructed with vertical orientation radio-opaque markers drilled through the central fossa of each pontic tooth which are precisely positioned perpendicular to the occlusal plane. A light-cured radio-opaque material is used to fin the vertical orientation material. Ridge crest orientation line is created and a radio-opaque coating is applied to the pontic teeth.

The resulting images from the CT-scan identify the exact image for each implant, the center and radiologic outline of each pontic tooth, and a true vertical reference for all the implants antero-posteriorly, and buccal-lingually. (Note: the terms antero-posterior and mesio-distal are used interchangably here.) These inter-related factors are superimposed on all the reformatted images which facilitates analysis, angular measurements, and transfer to the surgical guide.

Surgical Guide Fabrication

Surgical guide framework: An onlay type surgical guide is constructed from the radiographic guide as previously described.

Location of the osteotomy starting points: The cast is trimmed so that the occlusal plane is parallel with the base. This procedure guarantees that the cast is always oriented in the same way. The cast is positioned on the dual axis table with the base in the horizontal plane as in FIG. 3. The starting point of each osteotomy on the crest of the ridge is located by placing the original radiographic guide on the cast. The mandrill is lowered to the ridge crest mark in order to locate the exact center for the first implant. The radiographic guide is removed from the cast, without any cast movement, and a 701 drill placed into the drill press. The drill press is lowered to place a small hole into the stone cast equal in depth to the soft tissue gingival thickness taken from the actual cross sectional images. Since the vertical orientation pins are placed against the stone cast on the reformatted cross sectional image, the distance between the end of the orientation pin and the rest of the alveolar bone is the thickness of the gingiva. The process is repeated for the additional implant sites.

Surgical guide: A surgical guide is constructed on the stone cast from the radiographic guide by reproducing the starting point for each osteotomy at the crest of the residual ridge on the stone cast, and the individual antero-posterior and buccal-lingual inclination for each individual implant. The implant inclinations are accomplished by rotating the cast on the newly designed dual axis table described previously in the appropriate planes. The three dimensional orientation for each implant is used to position surgical steel drill guide tubes which are fixed to the surgical guide with self-curing resin. The steel drill guide tubes provide three dimensional guidance for the surgical procedures, correlating the occlusion with optimum implant location, orientation, and depth required by the anatomical topography.

CT Reformatted Images and Their Utilization

Panoramic image: The reformatted panoramic image reveals the angulation of the natural teeth in relation to the horizontal plane as viewed from the buccal side. This is important to prevent accidental damage to the root structure of the adjacent natural teeth.

Cross sectional images: Note should be taken of the fact that the software program of most CT scanners places the buccal on the left hand side of each cross sectional image, no matter which side is viewed.

Pontic orientation pin function: The superimposition of the vertical orientation pin into the reformatted images provides a way to 1) identify the specific cross sectional image for the implant, 2) the exact starting point of the osteotomy on the ridge, 3) the relationship of the compact bone and hazardous areas to that starting point, 4) and to clarify the biomechanical orientation of the implant to the occlusion. Thus, the starting point, mesio-distal and buccal-lingual inclination of each implant can be analyzed, measured, and reproduced in a surgical guide.

Three Dimensional Analysis of Implant Inclinations

CT-scan procedure—Orientation of the occlusal plane: In order to minimize distortion, it is important that the occlusal plane be perpendicular to the horizontal plane of the CT-scanner during the procedure and that the patient's head not be tilted to the left or right. To help accomplish this objective, a wooden tongue blade can be positioned between the posterior teeth on both sides of the arch, with the anterior portions extending extra-orally. This will help the technician's perspective to insure symmetrical head positioning as well as correct angulation. Faulty head placement results in linear distortion and possible cutting off of critical information, requiring the repetition of the CT scan.

Selecting the vertical level: It is also important to the technique that the technician include the occlusal portion of the radiographic guide in order to guarantee reproduction of the vertical orientation markers in the reformatted images. However, the scan should not be extended to the opposing jaw which may include metal restorations, or prostheses, that will cause scatter.

Implant orientation analysis: Cross-sectional and panoramic images are reproduced (and enlarged) with an in-office video camera or a 35 mm 4"×6" print. Vertical reference lines are drawn through the center of the images of the pontic orientation markers. The center line for the optimum orientation for each implant is drawn on the panoramic and cross sectional image reproductions. The resultant mesio-distal and buccal-lingual inclinations for each implant are measured with a protractor and recorded.

Buccal-lingual inclination (cross sectional image): A molar implant site on the patient's left side is illustrated in FIG. 1, which is a drawing of a CT reformatted cross sectional image taken from an actual CT-scan. Line A—A is drawn through the radiographic guide 5, then through vertical orientation pin 1 and through the crest of the alveolar bone 2. (In practice, the lines are drawn directly onto the CT-scan images. They are shown here drawn on the pictorial representation of the CT-scan for ease and clarity of representation.) This marks the center of the entrance point for the osteotomy. Line B—B is drawn from the osteotomy entrance point 2 through the residual alveolar bone 3 at the optimum implant orientation selected. The implant orientation is a diagnostic decision made by the clinician relative to compact bone, and the avoidance of anatomical hazards (not shown in FIG. 1) shown in the CT-scan. The angle "a" formed between A—A and B—B on the CT-scan (here shown on FIG. 1) is measured with a protractor and recorded, in this case at 16°. Therefore, the implant should be inclined lingually 16°. The optimum depth is obtained, utilizing the landmarks, and the scale 4 found on the images.

Figure 2:
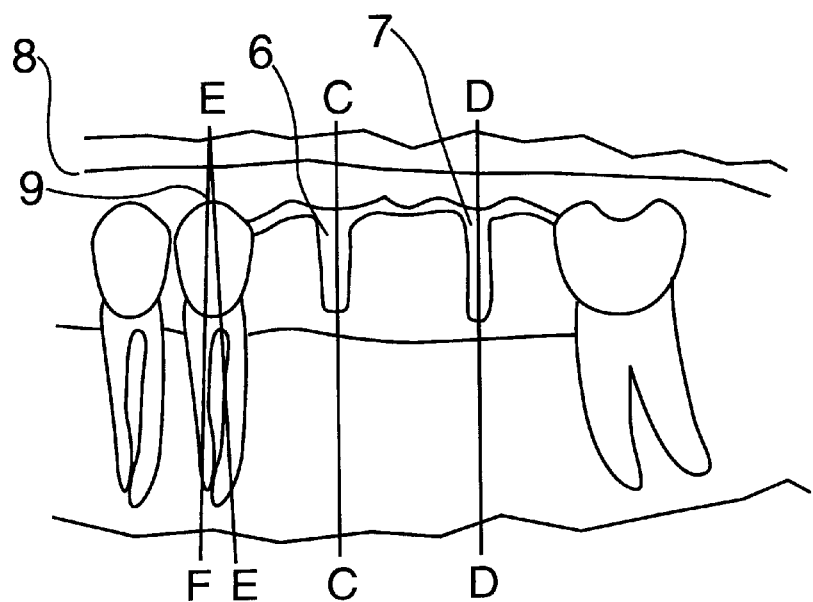
FIG. 2 is a drawing taken from a panoramic image showing orientation of adjacent teeth to the implant site and the angle deviation from vertical represented by that orientation.

Mesio-distal (antero-posterior) inclination: FIG. 2 is a drawing of a reformatted panoramic image of the patient's left side which includes the first and second molar implant sites. A vertical line C—C and D—D is drawn through each vertical orientation pin 6 and 7, respectively, which is perpendicular to the horizontal plane 8. A line E—E is drawn through the center of the natural bicuspid tooth 9, adjacent to the first molar implant, is inclined mesially when compared to a "true" vertical line E-F passing through the central fossa. Measurement with a protractor indicates that the implant should be inclined mesially 4° in order to be parallel to the adjacent bicuspid 9 to prevent accidental root perforation.

Buccal-lingual inclination: The first molar implant on the patient's left side requires lingual inclination of 16°. Reference to FIG. 3 shows a three dimensional guidance system 10 in the form of a drill press containing table 11 movable through all x-y directions about a point defined by drill press upper member 12 fixed in position relative to the table. In order to produce a given implant inclination, the table 11 is rotated in the appropriate direction via rotation knob 13 which is rotatable in either direction. For instance, the dual axis table is inclined bucally to produce a 16° lingual inclination of the implant.

Antero-posterior inclination: The first molar implant on the patient's left side should be inclined mesially 4° as previously described. The dual axis table 11 is inclined posteriorly, to produce a 4° mesial inclination of the implant in the saggital plane. This is achieved through rotation of rotation knob 14 which can rotate table 11 through the correct angles. The drill point 12 is able to drill into the stone cast model 15 over the starting point at the intersection between drill point 12 and the appropriate point in model 15. If done correctly, the starting point marking should be observed in the middle of the hole cut in the surgical guide.

In addition to providing rotational movement of the model 15 under the fixed point 12 via rotation about the axis controlled by rotation knob 13 and the axis about the rotational knob 14, table 11 is also provided with means to move the model 15 to virtually any point desired under point 12. This may be achieved in one aspect by providing moveable mounts 16, 17, 18, and 19 adapted to be slidably moved and affixed at any point around the periphery of table 11 secured respectively by securing nuts 20, 21, 22, and 23. The model 15 is then held in place by securing means 24, 25, 26, and 27, respectively.

Drill Guide Tube Placement

Transfer of starting points: Each implant requires individual three dimensional orientation, therefore the positioning of the drill guide tubes necessitates the replication of these respective angles on the dual axis table for each implant site. The starting point for each osteotomy is transferred to the drill guide tube, by first placing a pointed marker in the surgical steel drill guide tube. The drill guide tube is placed on a mandrill, and lowered in the drill press until the pointer fits into the starting point on the stone cast.

Transfer of orientation for each implant: Auto-curing resin fixes the drill guide tube to the surgical guide. The pointed marker is removed and the process repeated for the second molar implant site. The dual axis table is adjusted for the patient's right molar implant and the drill guide tube positioned in the same way. The drill guide tubes are shortened to be flush with the occlusal surface of the surgical guide. Mandrills have been placed in each surgical guide tube and photographed from the front view, in order to provide a perspective of the individuality of the lingual inclination of each implant. The surgical guide should be tried in intra-orally to insure stability before initiating the surgical procedures.

Surgical Procedure

Surgical procedure: The soft tissue is flapped and the surgical guide positioned. The surgical drill guide tubes, 1.6 mm o.d. facilitate the preparation of a 5 mm deep guided osteotomy at the specific mesio-distal, and buccal-lingual angulation planned at each implant site. The surgical guide is removed. The parallel walls of each pilot osteotomy serve as a guide for succeeding surgical procedures. Preferably, the newly designed set of drills as described in co-pending application Ser. No. 08/685,920 with a 3 mm non-cutting pilot extension maintains the precise pre-planned orientation of each pilot osteotomy while widening the preparation in 0.5 mm incremental steps. These newly designed end cutting drills provide adjustable stops that control the vertical depth without altering the planned implant orientation, although any standard bone drilling drills may be employed. The 5 mm deep, parallel walled guided osteotomy, becomes the pilot osteotomy for the remaining surgical procedures (left, FIG. 3).

Controlled depth preparation: The depth of the osteotomy should be 2 mm more than the implant length due to the difference in "end shape" of the implant (flat) compared to the bone drills ("V" shape), and to provide the surgeon with flexibility in determining the preferred anatomical relationship between the head of the implant and the crestal bone. The predetermined depth is set on the 1.6 mm end cutting drill and the osteotomy prepared to full depth for each implant site.

It should be emphasized that the first 5 mm of the parallel walled osteotomy provides pilot guidance for the full depth because the 1.6 mm drill is only end cutting. In order to accomplish this objective, any drills larger than the 1.6 mm are end cutting only on the periphery, and non-cutting in the central portion. This design resists accidental increases in depth.

Controlled width of osteotomy: The increase in diameter of he osteotomy is accomplished in 0.5 mm incremental increases to insure the maintenance of the pre-planned three dimensional orientation. Since each implant site may vary in depth, the widening procedure should be completed at one site before proceeding to the next. All the drills are set to the predetermined osteotomy depth at that site. Standard drills can be used without the new depth-fixing attachments, but such a process is technique-sensitive and time-consuming. In addition, standard end-cutters used to widen an osteotomy will tend to migrate from the original orientation.

Two step widening procedure: To insure the orientation of the osteotomy during the widening process, the drills described in U.S. Ser. No. 08/685,920 to provide a 3 mm non-cutting pilot extension, which maintains tracking (drill orientation), with a cutting edge of 0.5 mm wider in diameter. The non-cutting pilot extension must for best results always be the same diameter as the osteotomy it is tracking otherwise it will not maintain the orientation. However, the apical 3 mm of the osteotomy (corresponding to the 3 mm non-cutting pilot extension) will be 0.5 mm narrower requiring a second step for correction. This apical area is widened with an end-cutting drill with the same diameter as the coronal portion of the osteotomy. This latter end-cutter is used to the full length of the osteotomy, with the parallel walls of the coronal portion providing guidance. The two step 0.5 mm incremental widening procedure is continued with the next size larger pair of drills until the osteotomy diameter is correct for the implant selected.

Osteotomy tapped and beveled: When the osteotomy is in compact bone it is tapped. The osteotomy is counter sunk and the implant screwed into position. The instrumentation can be applied to cylindrical implants as well.

What is claimed is:

1. A method for locating optimal angles and depth of an osteotomy for insertion of a dental implant into a patient's jawbone which comprises, a) preparing a model of the patient's intended implant region and surrounding tooth structures, b) fitting said model with pontic teeth in proper occlusal relationship to form a pontic model, c) providing said pontic model with radio-opaque landmarks to form a radiographic guide which aids in determining the relationship of the pontic teeth to anatomic features of the patient, d) placing the radiographic guide onto the patient and taking a CT-scan, e) locating on said CT-scan the relevant dimensions, depth, and angles of the intended osteotomy and implant in consideration of the anatomical features revealed on the CT-scan, f) transferring said dimensions, depths, and angles to said model, g) placing said model on a table movable through three dimensions relative to a fixed drill point, h) drilling a hole through the pontic teeth at the angles determined from said CT-scan, said angles being obtained by manipulating the table through the three dimensions aforesaid, i) replacing the radiographic guide prepared in step h) onto said patient and drilling said implant osteotomy through said hole in said pontic teeth in step h) whereby the optimum angle, dimension, and depth of osteotomy as determined from the CT-scan is obtained on said patient.

2. The method of claim 1 wherein the pontic model is covered on the top thereof with a thin radio-opaque film.

3. The method of claim 2 wherein the pontic teeth has located therein a radio-opaque material oriented to be in a vertical position so that a true vertical orientation can be measured off the CT-scan.

4. The method of claim 1 wherein the model of step a) is a stone model.

5. The method of claim 1 according to step h) wherein ever widening drills are used to drill the osteotomy.

\* \* \* \* \*